United States Patent [19]
Cone

[11] Patent Number: 5,816,266
[45] Date of Patent: Oct. 6, 1998

[54] ELONGATED TOENAIL FILE AND METHOD OF USE

[76] Inventor: Richard R. Cone, 301 Kings Dr., Kings Mountain, N.C. 28086-9628

[21] Appl. No.: 805,669

[22] Filed: Feb. 27, 1997

[51] Int. Cl.$^6$ .................................................. A45D 29/04
[52] U.S. Cl. ............................................ 132/76.4; 132/200
[58] Field of Search ..................... 132/76.4, 76.5, 132/200; 451/523, 524, 525, 557

[56] References Cited

U.S. PATENT DOCUMENTS

| D. 123,291 | 10/1940 | Crompton | 132/76.4 |
|---|---|---|---|
| 132,468 | 10/1872 | Jacobsohn | 132/76.4 |
| 1,586,441 | 5/1926 | Blom | 132/76.4 |
| 1,829,338 | 10/1931 | Bynum | 132/76.5 |
| 2,479,514 | 8/1949 | Rucker | 132/76.4 |
| 2,566,688 | 9/1951 | West | 132/76.4 |
| 2,699,791 | 1/1955 | Hansen | 132/76.4 |
| 4,246,914 | 1/1981 | Keyser | 132/76.4 |
| 5,082,009 | 1/1992 | Cromer | 132/76.4 |
| 5,287,863 | 2/1994 | La Joie et al. | 132/76.4 |

FOREIGN PATENT DOCUMENTS

| 865969 | 4/1961 | United Kingdom | 132/76.4 |

*Primary Examiner*—Todd E. Manahan
*Attorney, Agent, or Firm*—Clifton Ted Hunt

[57] ABSTRACT

The elongated toenail file of this invention is a strip of material of a length sufficient to enable people to file their toenails while in a comfortable sitting position. A length of 18 inches has been found sufficient for this purpose. The front side of the toenail file has an abrasive surface for filing and the back side of the toenail file is smooth with transversely tapering portions terminating in thin longitudinal edges to fit comfortably between adjacent toes while filing.

4 Claims, 3 Drawing Sheets

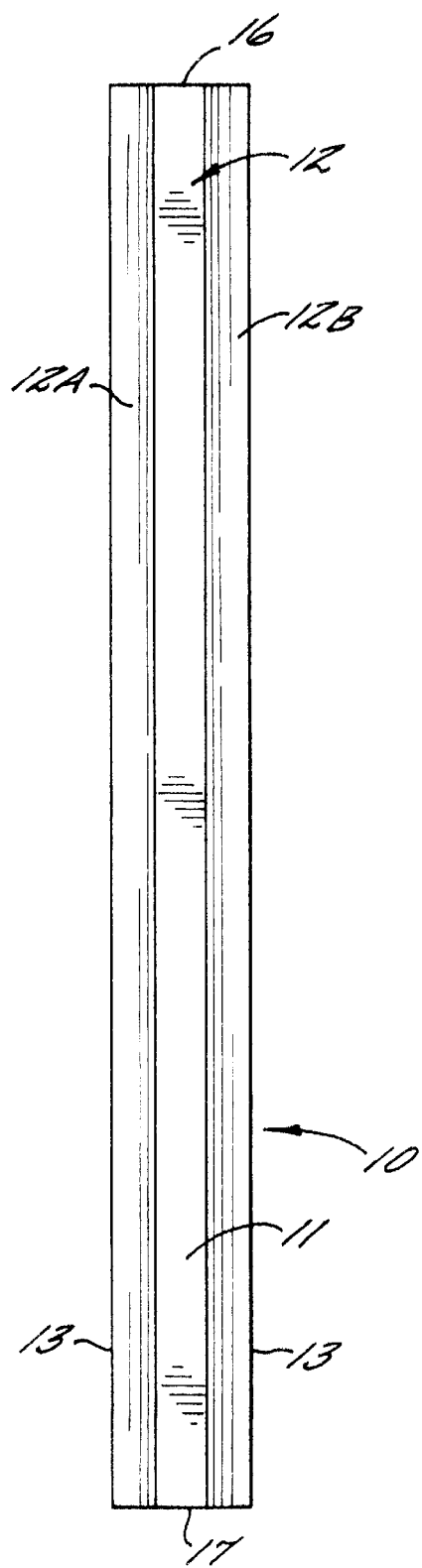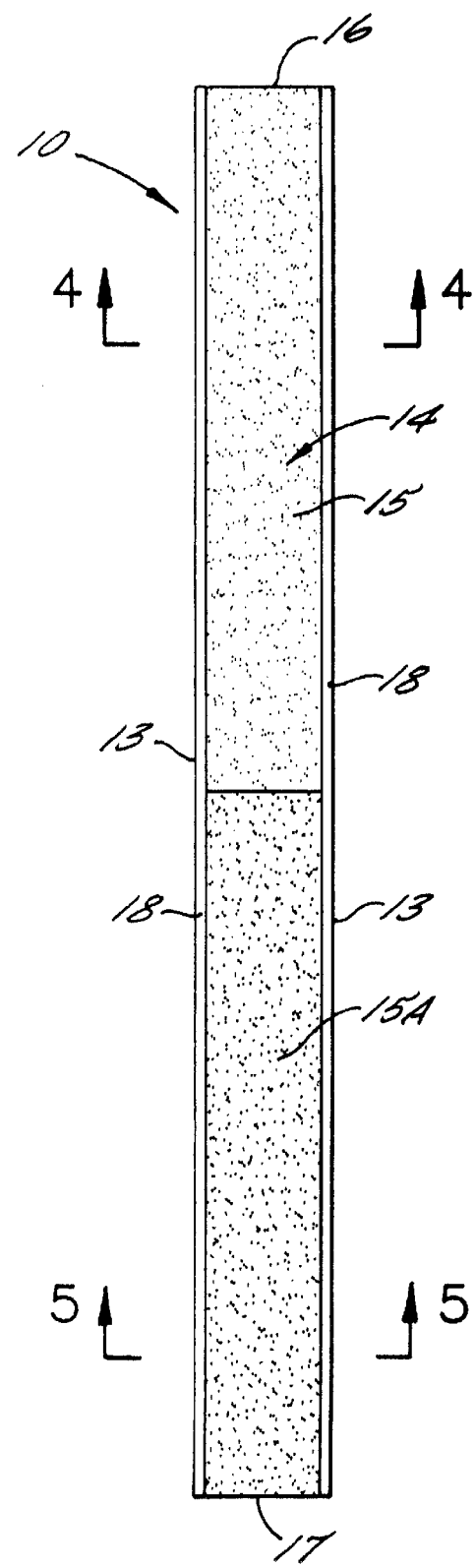
FIG. 2
FIG. 3

ELONGATED TOENAIL FILE AND METHOD OF USE

FIELD OF THE INVENTION

The present invention relates to a toenail file, and more particularly to the provision of elongated toenail files that make it possible for persons to file their toenails while in a comfortable sitting position, instead of in the usual squatting position.

BACKGROUND OF THE INVENTION

The filing of toenails is conventionally carried out with the same files that are used to file fingernails. As is well known, the usual fingernail file is formed with a filing or abrasive portion formed integrally with a short handle. The short handle is convenient and comfortable while filing fingernails but the short handle requires the user to bend over in a squatting position and stay in that uncomfortable position while applying the abrasive portion of the fingernail file to the toenails.

To applicant's knowledge, this problem has not been specifically addressed by the prior art. U.S. Pat. No. 4,246,914 issued Jan. 27, 1981 to Earl W. Keyser for ABRASIVE RELIEF DEVICE FOR THE FOOT is the most pertinent prior art known to applicant.

Keyser discloses the use of a file for the treatment of corns and callouses on the feet, not the filing of toenails. Keyser's file is a bar 13¼ inches in length and 2½ inches wide. One side of the bar is flat and smooth and the operative side has an arcuate cross sectional shape with an abraded surface at one end portion. Keyser shows a smooth depression at the other end portion of the operative side. The user places one foot firmly and supportively on the smooth depression so the file will remain stationary on the floor while the other foot is drawn across the abraded surface. There is no suggestion in Keyser of filing toenails.

SUMMARY OF THE INVENTION

The elongated toenail file of this invention is of a length sufficient to enable people to file their toenails while in a more comfortable position, while sitting. A length of 18 inches has been found generally sufficient for this purpose. The toenail file is made with a base, formed of wood, metal or plastic, and abrasive material, such as sandpaper, on the flat front side of the base.

The abrasive material is spaced inwardly from both longitudinal edges of the front surface of the base to expose the underlying smooth base and provide clean, smooth strips along the longitudinal edges that prevent the abrasive material from contacting and causing discomfort or injury to toes adjacent the toenail being filed. Smooth strips having a width of 1/32 or 0.030 of an inch (0.079 cm) have been found suitable for this purpose.

The other or back side of the toenail file is smooth with transversely tapered or chamfered portions flanking a flat mid-portion of relatively greater thickness. The thinner longitudinal smooth edges on the back side enable the toenail file to comfortably slide between two toes while filing.

BRIEF DESCRIPTION OF THE DRAWINGS

FIG. 2 is a plan view of the back side of the toenail file;

FIG. 2A is a plan view, partially in section, illustrating use of the toenail file;

FIG. 3 is a plan view of the front side of the toenail file;

DETAILED DESCRIPTION OF THE INVENTION

Figure 1:
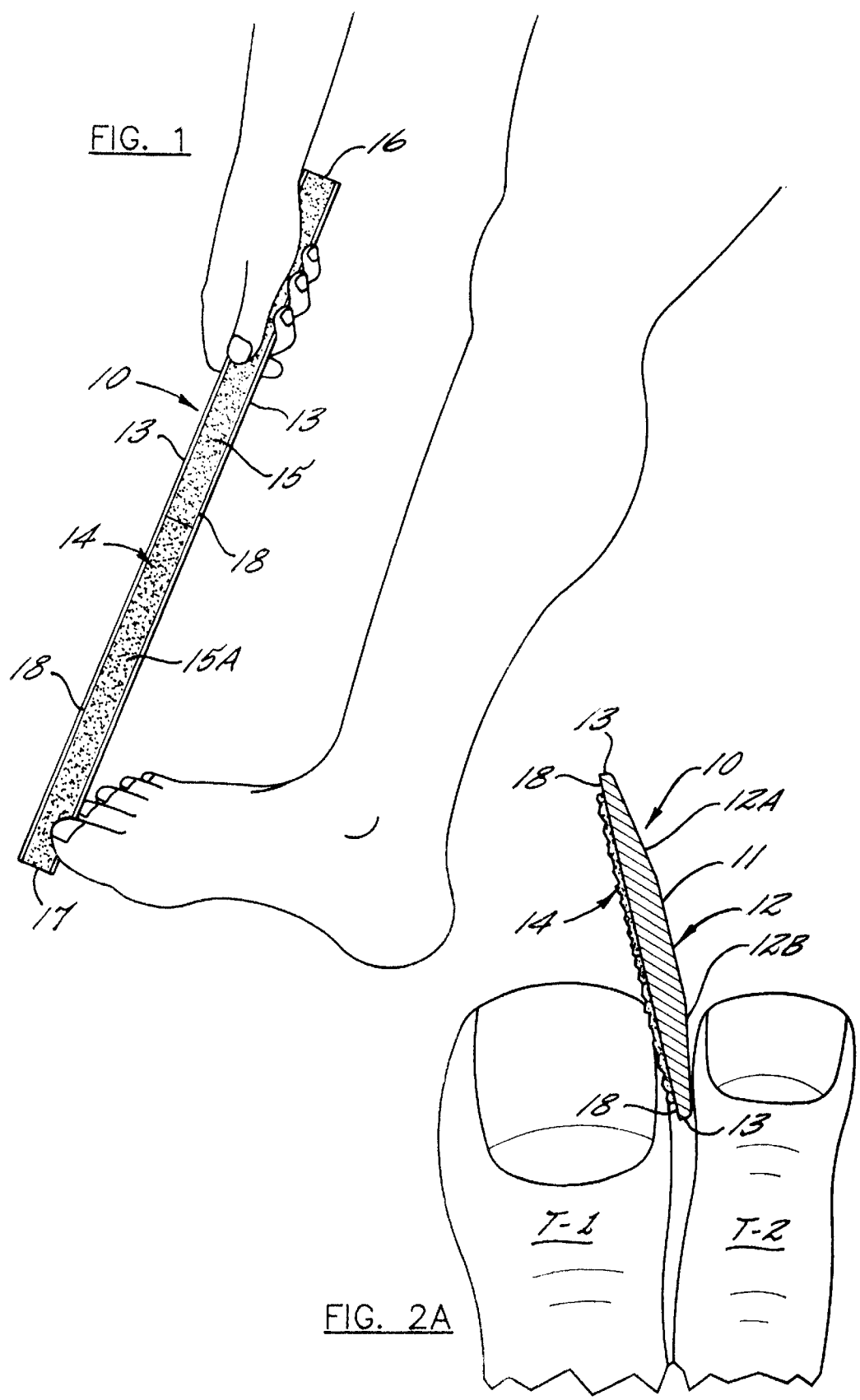
FIG. 1 is a perspective view of the elongated toenail file in use.
Figure 4:
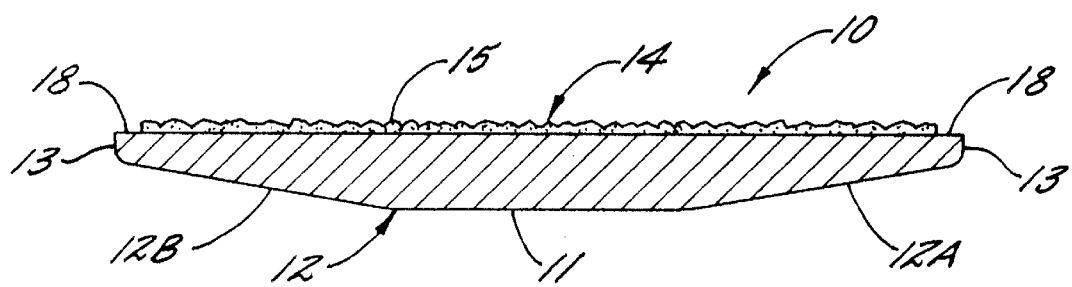
FIG. 4 is a sectional view taken substantially along the line 4—4 in FIG. 3.
Figure 5:
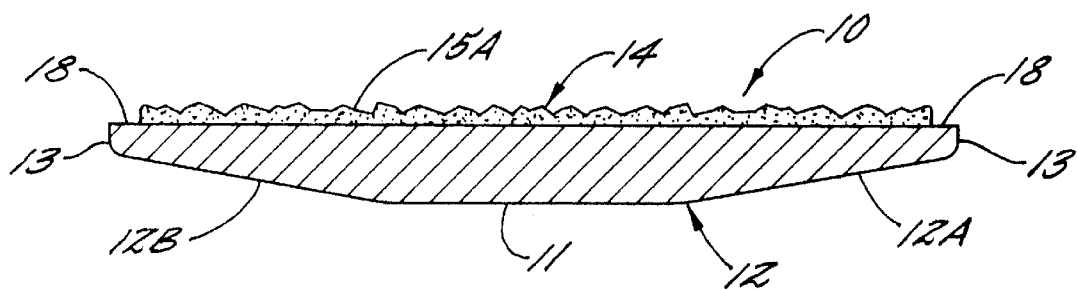
FIG. 5 is a sectional view taken substantially along the line 5—5 in FIG. 3.

Referring more specifically to the drawings, the elongated toenail file comprises a base 10 formed from an elongated strip of material, such as wood, metal or plastic. The base 10 is of a length approximating the distance between the knee and feet of the average person and suitable for a person to effectively file toenails while in a comfortable sitting position. A length of approximately 18 inches (45.7 cm) has been found satisfactory for this purpose, but the length is not critical and other lengths that are satisfactory for the intended purpose are within the spirit and scope of the invention. Any length between 12 and 24 inches is considered to be a satisfactory length for the base 10.

The width of the base 10 in the illustrated embodiment is approximately one inch (2.54 cm) and it has a thickness ranging from 3/16 inch (0.476 cm) throughout a flat mid-portion 11 on the back 12 of the base 10 to 1/16 inch (0.159 cm) along the longitudinal edges 13 of the toenail file. The length of the flat mid-portion 11 is flanked by transversely tapering portions 12A and 12B extending from the mid-portion 11 to the relatively thinner longitudinal edges 13.

The front side 14 of the base 10 is flat with an abrasive surface 15, formed of sandpaper or the like, for filing the toenails. A portion of the abrasive surface 15 may be of a different grit than the remaining portion, as indicated at 15A. The invention may be satisfactorily carried out with an abrasive surface of the same grit applied throughout the front surface 14; or with an abrasive surface of desired grit(s) extending sufficiently inwardly from one or both ends 16 and 17 of the base 10 for filing toenails.

In any event, it is preferred for the comfort and safety of the user that the abrasive surface on the front of the base be spaced inwardly from the longitudinal edges of the base to provide clean smooth strips 18 between the edges of the abrasive surface and the edges of the base. The width of the smooth strips 18 is not critical but a width of approximately 1/32 or 0.030 of an inch (0.079 cm) has been found sufficient to prevent the abrasive surface from undesirably contacting adjacent toes while filing a toenail.

Operation

The toenails may be filed while the user is in a sitting position with one end of the toenail file 10 held approximately half way between the knee and the toenails being filed. The foot having the toenails being filed is preferably elevated as by resting the heel of that foot on the floor.

The toenails are filed by reciprocating an abrasive surface 15 or 15A of the toenail file 10 against successive toenails. Reciprocation of the toenail file while filing the fronts of the toenails often brings a longitudinal edge 13 of the toenail file against an adjacent toe that is longer than the toe on which the toenail is being filed. The smooth strips 18 contact the adjacent toes instead of the abrasive surface 15 or 15A, thereby avoiding discomfort or injury.

While filing the end portions of toenails that are next to adjacent toenails, the toenail file 10 is reciprocated between two toes T-1 and T-2 while filing the toenail T-1 (FIG. 2A). Only the tapered or chamfered portion 12A (or 12B) need extend between the toes while one toenail is being filed with an abrasive surface of the toenail file. The smooth, thin portion 12A of the back side 12 is reciprocated beside the adjacent toe T-2 while the abrasive surface 15 or 15A is reciprocated against the toenail on toe T-1 as it is being filed. The smooth thin portions 12A and 12B on the back of the base 10 enable the toenail file to be effectively reciprocated between the toes without uncomfortably chafing a toe adjacent the toenail being filed.

There is thus provided a toenail file that can be efficiently used to file toenails while in a sitting position. Although specific terms have been used in describing the invention, they have been used in a generic and descriptive sense only and not for the purpose of limitation.

Modifications of the toenail file may be made without departing from the spirit of the invention, if made within the scope of the following claims to invention.

I claim:

1. A toenail file comprising:

a base formed from an elongated strip of material approximately 18 inches long and having a front side, a back side, relatively thin longitudinal edges and opposing ends;

the back side of the base being smooth and including a mid-portion flanked by transversely tapering portions extending from the mid-portion to the relatively thin longitudinal edges; and an abrasive surface on the front side of the base, whereby a person may hold the base in one hand while in a sitting position and file the toenails by reciprocating the abrasive surface against successive toenails.

2. A toenail file comprising:

a base formed from an elongated strip of material having a front side, a back side, opposed ends and relatively thin longitudinal edges extending between the ends of the base;

an abrasive surface on the front side of the base, the abrasive surface terminating at the ends of the base and being spaced inwardly from the longitudinal edges of the base; and the back side of the base being smooth and including a mid-portion flanked by chamfered portions extending from the mid-portion to the relatively thin longitudinal edges.

3. The invention of claim 2 wherein the length of the base is 18 inches.

4. A method of filing toenails which comprises the steps of:

providing an elongated base formed from a strip of rigid material having opposed ends, and an abrasive surface extending the full length of the base;

grasping the base at any place along its length that makes it possible to comfortably reach the toes with one end portion of the base while in a sitting position; and rubbing the abrasive surface on said one end portion of the base against successive toenails while in a sitting position.

* * * * *